United States Patent
Pieper et al.

(10) Patent No.: US 8,681,247 B1
(45) Date of Patent: Mar. 25, 2014

(54) FIELD FLATTENING CORRECTION METHOD FOR FLUORESCENCE IMAGING SYSTEM

(75) Inventors: Sean B. Pieper, Lincoln, NE (US); Christopher J. Lesiak, Lincoln, NE (US); Ahmed Bouzid, Lincoln, NE (US)

(73) Assignee: Li-Cor, Inc., Lincoln, NE (US)

( * ) Notice: Subject to any disclaimer, the term of this patent is extended or adjusted under 35 U.S.C. 154(b) by 441 days.

(21) Appl. No.: 13/106,758

(22) Filed: May 12, 2011

Related U.S. Application Data

(60) Provisional application No. 61/334,080, filed on May 12, 2010.

(51) Int. Cl.
| | | |
|---|---|---|
| *H04N 5/217* | (2011.01) | |
| *H04N 17/00* | (2006.01) | |
| *H04N 9/73* | (2006.01) | |
| *H04N 5/222* | (2006.01) | |
| *G01J 3/30* | (2006.01) | |
| *F21V 9/16* | (2006.01) | |
| *A61B 6/00* | (2006.01) | |

(52) U.S. Cl.
USPC ........ 348/241; 348/370; 348/224.1; 348/187; 356/317; 250/458.1; 600/473

(58) Field of Classification Search
USPC ........... 348/187, 241, 370, 371, 222.1, 224.1, 348/225.1; 356/317, 318; 600/746, 473; 362/259, 260; 250/458.1, 459.1
See application file for complete search history.

(56) References Cited

U.S. PATENT DOCUMENTS

| | | | | |
|---|---|---|---|---|
| 5,865,754 | A * | 2/1999 | Sevick-Muraca et al. | 356/317 |
| 7,286,232 | B2 * | 10/2007 | Bouzid | 356/417 |
| 7,729,750 | B2 * | 6/2010 | Tromberg et al. | 356/317 |
| 8,014,569 | B2 * | 9/2011 | Durkin et al. | 356/337 |
| 2002/0072677 | A1 * | 6/2002 | Sevick-Muraca et al. | 600/473 |
| 2008/0269617 | A1 * | 10/2008 | Kohler et al. | 600/476 |
| 2009/0080194 | A1 * | 3/2009 | Bouzid et al. | 250/459.1 |
| 2011/0042580 | A1 * | 2/2011 | Wilson et al. | 250/458.1 |

* cited by examiner

*Primary Examiner* — Nhan T Tran
(74) *Attorney, Agent, or Firm* — Gerald T. Gray; Leydig, Voit & Mayer, LLP

(57) ABSTRACT

Systems and methods for flattening the image across the entire field by correcting the image for both the fluorescence and scatter spatial variations. Images of a stable fluorescence target and a scattering target are separately acquired in an imaging system. From these target images, a pixel remapping function, e.g., including two correcting pixel slopes, is calculated for subsequent image pixel remapping. An image of a sample under investigation is then acquired by the imaging system and the sample image is remapped based on the pixel remapping function for the imaging system to form a corrected (field flattened) image. Which correction pixel slope to be used is determined based on whether a sample image pixel value is higher or lower than a threshold value.

20 Claims, 5 Drawing Sheets

Plot indicating how a pixel correction mapping is performed using a dual correction method.

Example of fluorescence field flattening using a dual correction method imaging fluorescent target without and with the design of the invention.

Example of fluorescence field flattening using a dual correction method imaging a scattering target without and with the design of the invention.

FIELD FLATTENING CORRECTION METHOD FOR FLUORESCENCE IMAGING SYSTEM

CROSS-REFERENCES TO RELATED APPLICATIONS

This application claims the benefit of U.S. Provisional Application Ser. No. 61/334,080, filed May 12, 2010, the disclosure of which is incorporated herein by reference in its entirety.

BACKGROUND

The present invention relates generally to fluorescence imaging, and more particularly to field flattening in fluorescence imaging.

Fluorescence imaging typically includes illuminating a dye-labeled target with light having wavelength content that matches, at least partially, the absorption spectrum of a fluorescence dye and imaging the target with an optical system that favors the emitted fluorescence light over any reflected or scattered portion of the excitation light. As with any other fluorescence imaging system the amount of light that reaches the image plane, and hence a detector, for a given amount of fluorescent dye concentration at the target plane varies spatially. The three key components for this variation can be expressed by the following equation:

$$S_{Pixel}(P,t,x,y) = [S_{Fl}(P,t,x,y) + S_{Scatter}(P,t,x,y)]$$

where $S_{pixel}(P,t,x,y)$ is the amount of light arriving at a pixel of a detector such as a CCD. $S_{Fl}(P,t,x,y)$ is the fluorescence signal from a desired dye-labeled target and varies at low concentrations linearly with the power of the excitation light, P, detector exposure time, t, and varies spatially with the excitation spatial distribution as well as the response of the imaging system, x and y. $S_{scatter}(P,t,x,y)$ is the amount of scattered light reaching a pixel comprised primarily of excitation light varying linearly with excitation light, P, detector exposure time, t, and can vary spatially with the excitation spatial distribution, system components scattering excitation light, etc. as well as the response of the imaging system, x and y. This scattered light could also encompass other sources of light such as photoluminescence of objects/materials in the instrument that exhibit auto-fluorescence and/or scatter light when exposed to the excitation light. Other contributions that affect the spatial variation of light impinging on a pixel is the typical radiative falloff that all imaging systems experience of $\cos^4 \theta$, where $\theta$ is the angle between image point, or pixel, and the optical axis (center line through the optical system) and is easily corrected for with an electronics detector array such as a CCD-based imaging system. Vignetting is another factor that, if present, will also impact the pixel signal value whose influence would exhibit typically as a faster rate of radiative falloff in the image plane with increasing $\theta$.

To accurately quantitate a desired dye-labeled target at some concentration the image pixel signal reported needs to be constant for that amount of fluorescent dye everywhere across the field of view. Thus, the same signal level is reported whether the target is placed at the center of the object plane or at the extremities of the imaged field of view. This requires knowledge of the imaging system's spatial signal response. Normally the fluorescence signal dominates and can be limited in detectability by the electrical background of the detection system at short exposure lengths. At longer exposure lengths, the electrical noise becomes smaller than the scattered light signal allowing the spatial variation of this component to be observed. At these longer exposure lengths, pixel signal is dominated by fluorescence at higher light levels with scattered light becoming dominant at lower light levels resulting in a non-uniform spatial system response.

Spatial variation of the fluorescence light can be minimized by employing a methodology for obtaining uniform excitation illumination of the target area over the object plane of the imaging system as described in patent application publication 2009/0080194 A1, which is hereby incorporated by reference. Minimizing the contribution of scattered light can be accomplished by ensuring the imaging or detection system efficiently filters out excitation light. This can be achieved by employing a filtering strategy as described in U.S. Pat. No. 7,286,232, which is hereby incorporated by reference. Employing good practices as these will tend to result in the fluorescence spatial variation to be radially symmetric about the center of the image. However, the spatial variation due to scatter will likely not be symmetric, depending more on system configuration and components that light scatters from.

Nonetheless, it is desirable to provide systems and methods for flattening the image across the entire field by correcting the image for both the fluorescence and scatter spatial variations.

Therefore it is desirable to provide systems and methods that overcome the above and other problems.

BRIEF SUMMARY

The present invention provides systems and methods for flattening the image across the entire field by correcting the image for both the fluorescence and scatter spatial variations. The embodiments disclosed herein are particularly useful in situations where the auto-fluorescence of the target is low and long exposures are required is addressed, such as, for example, for imaging western blots on membranes, gels, and glass media.

Imaging in the near-IR wavelength range is becoming the focus of much scientific work because of low auto-fluorescence of tissue and other sample-holding media at longer and longer exposure lengths to observe smaller amounts of dye concentrations. This places ever increasing demands on the performance of imaging systems to the point that performing a simple field correction using a fluorescent target is no longer sufficient. The embodiments disclosed herein advantageously maximize system performance in cases where scattered light becomes a notable contributor to the signal detected in a fluorescent image, thereby maximizing the information that scientists can use.

Images of a stable fluorescence target and a scattering target are separately acquired in an imaging system. From these target images, a pixel remapping function, e.g., including two correcting pixel slopes, is calculated for subsequent image pixel remapping. An image of a sample under investigation is then acquired by the imaging system and the sample image is remapped based on the pixel remapping function for the imaging system to form a corrected (field flattened) image. Which correction pixel slope to be used is determined based on whether a sample image pixel value is higher or lower than a threshold value.

According to one embodiment, a method is provided for use in flattening an image across a usable field of view in an imaging system having an illumination source configured to illuminate a sample platform with illumination at a first frequency and a detector system having a detector that detects illumination at a second frequency by correcting the image for fluorescence spatial variations and scatter spatial variations. The method typically includes acquiring a first image of a stable fluorescent target located proximal to the sample platform using the detector, wherein the stable fluorescent target absorbs illumination at said first frequency and emits at said second frequency and has a size that fills at least a usable field of view of the detector system, and acquiring a second image of a scattering target located proximal to the sample platform using the detector, wherein the scattering target scatters illumination at said first frequency and has a size that fills at least the usable field of view of the detector system. The method also typically includes determining a pixel remapping function based on the acquired first and second images and storing the pixel remapping function for later use in correcting for fluorescence spatial variations and scatter spatial variations in images of a sample taken using the imaging system. In certain aspects, the method further includes acquiring an image of a sample located proximal to the sample platform, and thereafter adjusting, on a pixel-by-pixel basis, an intensity value of each pixel in the image of the sample using the pixel remapping function to form a corrected image. In certain aspects, the method further include displaying a representation of the corrected image, e.g., on a display device.

According to another embodiment, a method is provided for flattening an image across a usable field of view in an imaging system having an illumination source configured to illuminate a sample platform with illumination at a first frequency and a detector system having a detector that detects illumination at a second frequency. The method typically includes acquiring an image of a sample located proximal to the sample platform using the detector, accessing stored pixel remapping data for the imaging system, wherein the remapping data includes a mapping function that corrects for fluorescence spatial variations and scatter spatial variations in images taken using the imaging system based on the intensity value of a pixel, and adjusting, on a pixel-by-pixel basis, an intensity value of each pixel in the image of the sample using the pixel remapping data to form a corrected image. In certain aspects, the method further include displaying a representation of the corrected image, e.g., on a display device. In certain aspects, the stored pixel remapping data is determined by acquiring a first image of a stable fluorescent target located proximal to the sample platform using the detector, wherein the stable fluorescent target absorbs illumination at said first frequency and emits at said second frequency and has a size that fills at least a usable field of view of the detector system, by acquiring a second image of a scattering target located proximal to the sample platform using the detector, wherein the scattering target scatters illumination at said first frequency and has a size that fills at least the usable field of view of the detector system, and by determining the pixel remapping function based on the acquired first and second images.

According to yet another embodiment, an imaging system is provided that typically includes a sample platform, an illumination source configured to illuminate the sample platform with illumination at a first frequency, and a detector system including a detector element that detects illumination at a second frequency. The system also typically includes a memory that stores pixel remapping data for the imaging system, wherein the remapping data includes a mapping function that corrects for fluorescence spatial variations and scatter spatial variations in images taken using the imaging system based on the intensity value of a pixel. The system also typically includes an intelligence module, e.g., a processor, adapted to receive and process signals from the detector element, wherein during operation, the detector element acquires an image of a sample located proximal to the sample platform, the intelligence module accesses the stored mapping function and adjusts, on a pixel-by-pixel basis, an intensity value of each pixel in the image of the sample using the pixel mapping function to form a corrected image. In certain aspects, the detector element includes one of a single pixel detector, a single dimension array detector or a two dimensional array detector such as a CCD array detector. In certain aspects, the stored pixel remapping data is determined by acquiring a first image of a stable fluorescent target located proximal to the sample platform using the detector, wherein the stable fluorescent target absorbs illumination at said first frequency and emits at said second frequency and has a size that fills at least a usable field of view of the detector system, by acquiring a second image of a scattering target located proximal to the sample platform using the detector, wherein the scattering target scatters illumination at said first frequency and has a size that fills at least the usable field of view of the detector system, and by determining the pixel remapping function based on the acquired first and second images.

In certain aspects, the pixel remapping function is a piecewise continuous function having first and second linear slopes meeting at a threshold value, wherein adjusting includes using the first slope to modify the pixel value if the intensity value of the pixel is below the threshold value, and using the first slope to modify the pixel value if the intensity value of the pixel is above the threshold value.

A detector system typically includes optical elements configured to direct and focus light emitted from or scattered by the sample platform onto a detector. In certain aspects, the detector includes one of a single pixel detector, a single dimension array detector or a two dimensional array detector such as a CCD array detector.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

DETAILED DESCRIPTION OF THE INVENTION

The present invention provides systems and methods for flattening the image across the entire field by correcting the image for both the fluorescence and scatter spatial variations.

Figure 1:
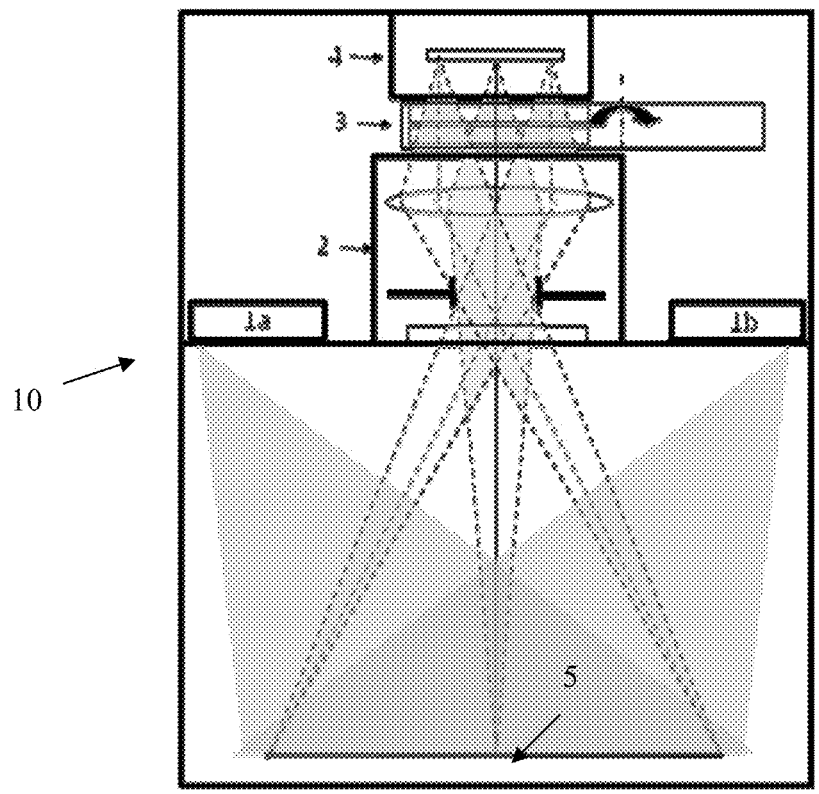
FIG. 1 illustrates a fluorescence imaging system according to one embodiment

A fluorescence imaging system 10 according to one embodiment is shown in FIG. 1. System 10 includes at least one illumination source (two sources 1a and 1b are shown). Typically an illumination source includes a laser, however, other illumination sources may be used as desired. In one embodiment, an illumination source includes a laser diode device that is configured to emit at a desired wavelength (or frequency) (e.g., 680 nm or 780 nm) and is configured to illuminate platform 5, or a sample on platform 5. The laser sources are typically packaged with appropriate cooling elements and optical elements to direct their output onto platform 5. Light from platform 5 is directed and focused by imaging optics 2 onto detector 4, e.g., a CCD detector or other detector. Optional filter elements 3 are provided to facilitate filtering of the light that reaches detector 4. In certain aspects, system 10 is enclosed within a structure, such as a light-tight housing structure.

For example, in certain embodiments, the imaging system 10 may include a CCD-based imaging system configured in a telecentric imaging and filtering architecture, such as described in U.S. Pat. No. 7,286,232, which is hereby incorporated by reference in its entirety. It is preferred to configure the illumination according to US Patent Application publication No. 2009/0080194, which is hereby incorporated by reference in its entirety.

System 10 also includes an intelligence module (not shown), such as one or more processors, that is communicably coupled with the detector 4. The intelligence module is adapted to receive and process signals from detector 4, e.g., signals representing, or proportional to, the detected illumination within the detector's detection bandwidth. The intelligence module may automatically process the data and signals as received, or it may receive the data and signals and process subsequently, e.g., in response to a user command. An optional display device (not shown) is provided in certain embodiments to display data representative of various signals and images captured and/or processed by system 10. A memory module or device can also be provided to store data and code for use by the intelligence module, or for another system. For example, the memory may store code, executable by a processor, for implementing methods as disclosed herein, and/or data from the detectors and/or processor may be stored thereon. For example, pixel remapping data as discussed herein may be stored to the memory for later access and use by the intelligence module as described herein. The memory may include a RAM or ROM, hard disk or any portable, non-transitory medium such as a DVD or CD.

Figure 2:
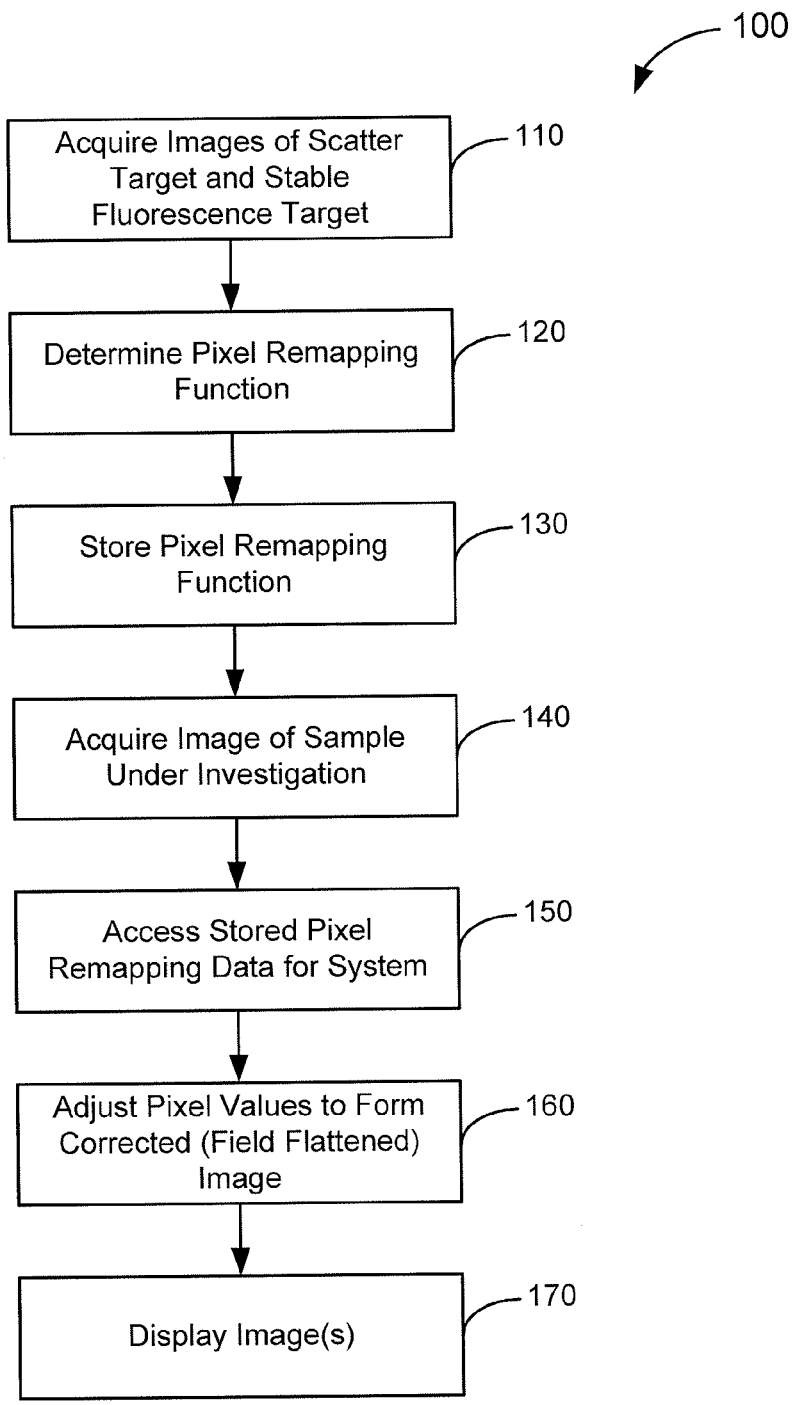
FIG. 2 illustrates a method for flattening an image across a usable field of view in an imaging system according to one embodiment.

FIG. 2 illustrates a method 100 for flattening an image across a usable field of view in an imaging system such as system 10. According to one embodiment, a stable fluorescence target and a scattering target are provided for use in performing the method. The stable fluorescence target should be of sufficient size to at least fill the imaging system's usable field of view and is excited by the imaging system's excitation source(s) and emits light in the preferred wavelength band of the detection system. As used herein, a "stable" fluorescence target means that it does not change over time, or at least its rate of fluorescence emission in response to the same amount of excitation light stays nearly constant over time. Examples of stable fluorescence targets include absorption glass, such as RG780 and RG1000 made by Schott. The scattering target should of sufficient size to at least fill the imaging system's usable field of view and preferably has both scattering and low auto-fluorescence characteristics. When exposed to the imaging system's excitation source(s) the scattered light should closely resemble a lambertian ($I(\theta)=I_o \cos \theta$) distribution and be of a similar light level as seen in the imaging system as the limiting media of the imaging system (e.g. sample holding plate, membrane, etc.) such as an appropriate reflectance value of Spectralon® (www.labsphere.com).

In step 110, an image of each target is separately acquired. For example, the fluorescence target is positioned proximal the platform and an image acquired while being illuminated by the illumination source at a first frequency. The stable fluorescent target absorbs illumination at the first frequency and emits at a second frequency detectable by the detector. Similarly, the scatter target is positioned proximal the platform and an image acquired while being illuminated by the illumination source at a first frequency, before or after acquisition of a fluorescence target image. The scatter target scatters illumination at the first frequency. In one embodiment, multiple (e.g., 6) replicate images of each target are obtained, and then for each pixel in each stack of target images a trimmed mean is obtained. The trimmed mean is the result of discarding one or more of the maximum and minimum values and taking a mean of the remaining values, where the mean image of each target is used in step 120.

In step 120, from these target images (either single images or mean images), two correcting pixel slopes are calculated for subsequent image pixel remapping. In one embodiment, to determine the pixel remapping function, a target image (or target mean image) first has a background (dark) image subtracted from it, on a pixel-by pixel basis. One method for determining this dark image is described in copending application Ser. No. 13/106,740, filed on May 12, 2011, titled: WIDE DYNAMIC RANGE IMAGING, and claiming priority from provisional application Ser. No. 61/334,109, filed May 12, 2010), the disclosures of which are incorporated herein by reference in their entirety. The result of dark image subtraction results in target image "A". Target image "A" is the low-pass filtered, resulting in target image "B". Target image "A" is clipped at a multiple (m) of "B", resulting in a target image "C". This multiplier (m) is one embodiment is 2. Image "C" is at most 2m brighter than "B". Image "C" is low pass filtered giving target image "D". The remapping function is then calculated by dividing a constant (which may be the mean pixel value of "D") by each individual pixel of "D". This methodology is performed for both the scattering and fluorescent corrections; the difference is which image is input. It is important that the result be tolerant of noise and specs of dust on the calibration target; the clipping and low pass filtering solves that. The low pass filter is also useful to correct the low frequency non-uniformity of the field. In step 130, the pixel remapping data is stored to memory.

In step 140, a sample, such as a fluorescence sample, is placed proximal to the sample platform and an image of the sample is acquired, e.g., while being illuminated by the illumination source at a first frequency. In step 150, the pixel remapping data is accessed and in step 160, pixel values of the acquired sample image are adjusted, e.g., using the pixel correcting slopes, on a pixel-by-pixel basis, to form a field flattened image. Determining which correction pixel slope to be used is determined based on whether a pixel value is higher or lower than a threshold value. In step 170, the field flattened image is displayed, e.g., on a display device. It should be appreciated that steps 110 through 130 may be implemented apart from steps 140 through 170. For example, upon manufacture and calibration of an imaging system, steps 110 through 130 may be performed so that the imaging system has stored thereon the Pixel remapping data for later use.

Figure 3:
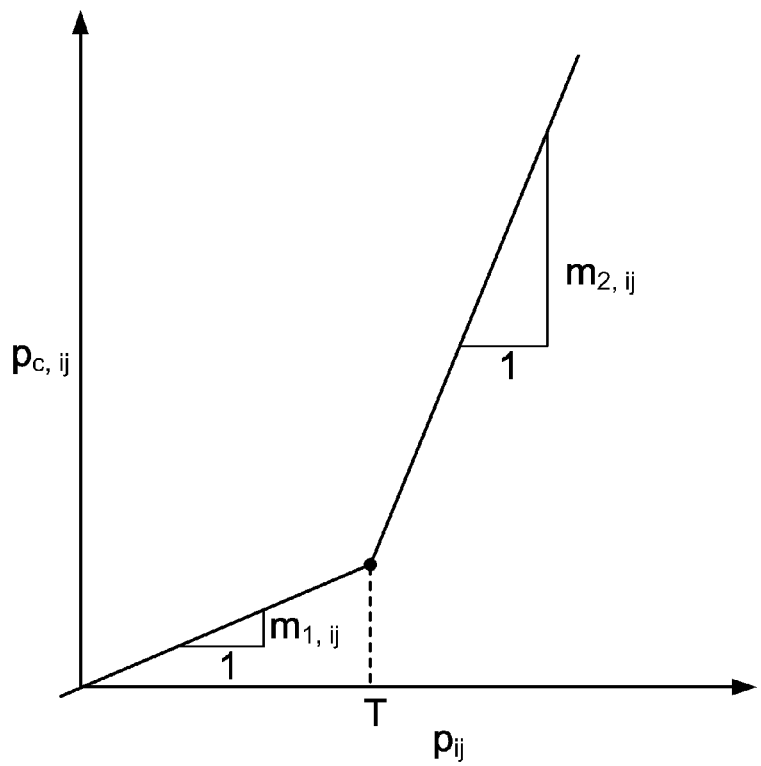
FIG. 3 shows a representation of the mapping of a pixel, where $p_{ij}$ is the uncorrected pixel value and $p_{c,\,ij}$ is the corrected pixel value.

FIG. 3 shows a representation of the mapping of a pixel, for example, as performed in step 160, where $p_{ij}$ is the uncorrected pixel value and $p_{c, ij}$ is the corrected pixel value. The pixel correction is described by the piecewise equation:

$$P_{c,ij} = \begin{cases} m_{1,ij} p_{ij} & \text{if } p_{ij} \leq T \\ m_{2,ij}(p_{ij} - T) + m_{1,ij} & \text{if } p_{ij} > T \end{cases}$$

$$m_{1,ij} = \frac{\sum_{i=1}^{n} \sum_{j=1}^{m} p_{Sc,ij}}{nm p_{Sc,ij}} = \frac{\overline{p_{Sc,ij}}}{p_{Sc,ij}}$$

$$m_{2,ij} = \frac{\sum_{i=1}^{n} \sum_{j=1}^{m} p_{Fl,ij}}{nm p_{Fl,ij}} = \frac{\overline{p_{Fl,ij}}}{p_{Fl,ij}}$$

which form of the equation is used to correct each pixel is decided based upon the pixel's value with respect to a threshold, T. This threshold, T, can be based on the mean image value of the scatter target. The actual value of threshold, T, can be scaled from the mean scatter image value either higher or lower. $\overline{p_{Sc,ij}}$ and $\overline{p_{Fl,ij}}$ are the mean image value over all pixels for the scattering and fluorescence targets respectively. Subscripts Sc and Fl representing the pixel value of the scattering and fluorescent targets. The total number of pixel rows and columns are represented by n and m respectively with i and j as pixel position representing the ith row and jth column. This notation accommodates a 2-D array such as a CCD but can be simplified to a 1-D detector array or even a single pixel detector that is mechanically moved to build an image.

Figure 4:
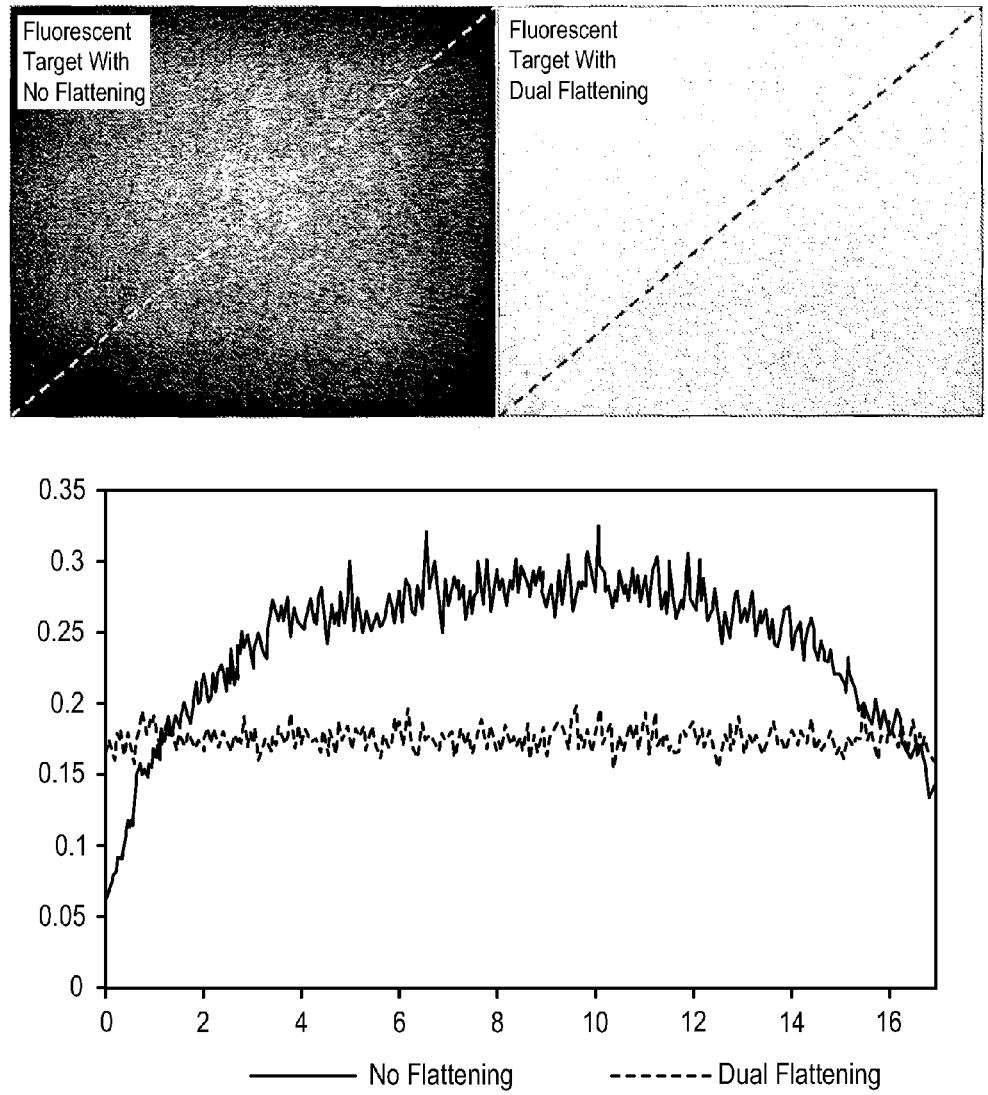
FIG. 4 shows an example of fluorescence imaging over the field of a suitable fluorescence target before and after field flattening with 30 seconds exposure length
Figure 5:
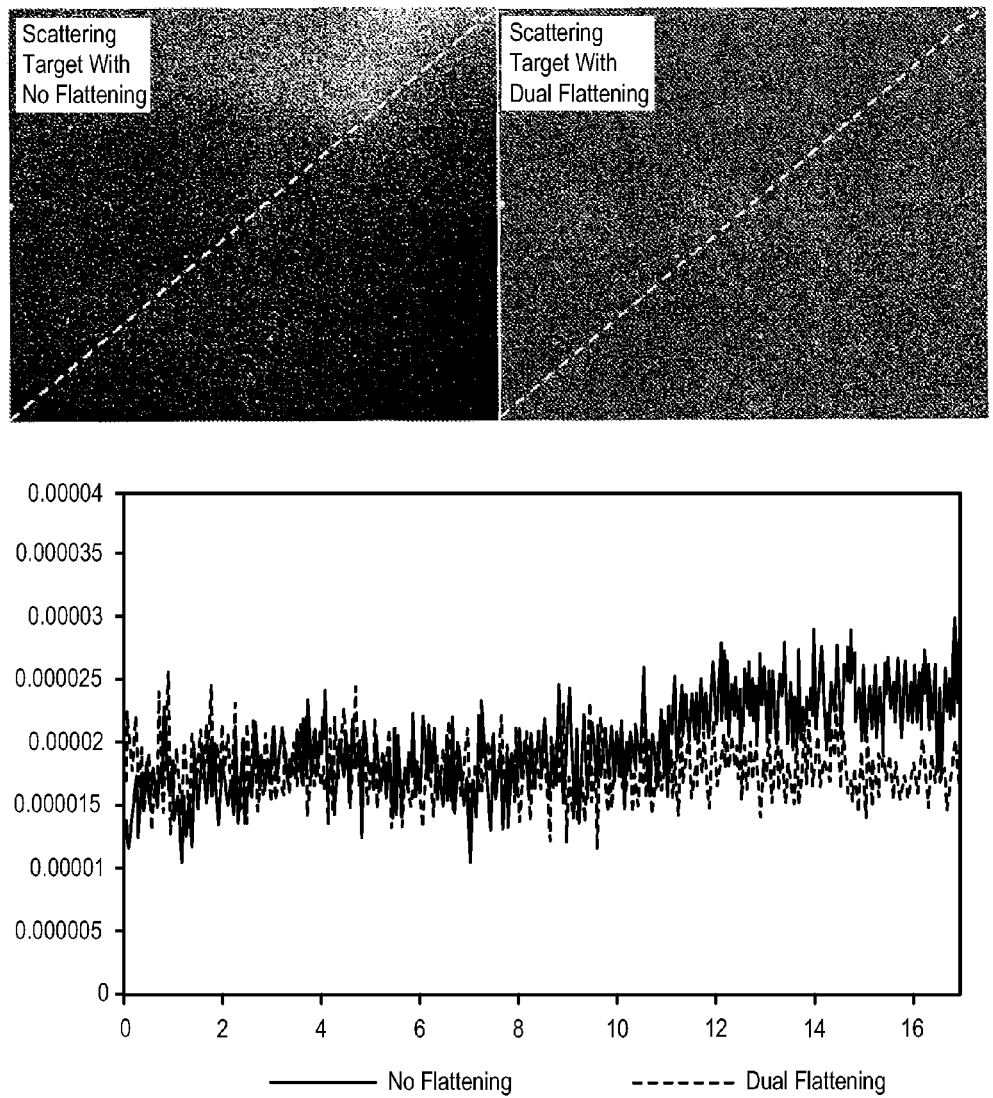
FIG. 5 illustrates an example of a fluorescence image of a suitable scattering target with a 10 minute exposure length before and after field flattening.

Test Results with Embodiment Described Above:

FIG. 4 shows an example of fluorescence imaging over the field of a suitable fluorescence target before and after field flattening with 30 seconds exposure length. An example of a fluorescence image of a suitable scattering target with a 10 minute exposure length is shown in FIG. 5 before and after field flattening. As expected, the fluorescence spatial variation seen in the before image of FIG. 4 shows a strong radial symmetry, also as expected the before scatter image in FIG. 5 exhibits a non-symmetric pattern. A profile plot for each target before and after field flattening is applied is also shown for both targets. The plot is from the lower left corner to the upper right corner represented by the diagonal dashed line on each image. It can be clearly seen that the image is much more uniform across the field after a method of the invention is applied to an acquired image with uniformity improving by up to 5x. But most importantly the image of low fluorescence light levels where scattering is a major contributor the non symmetric spatial response is greatly improved.

While the invention has been described by way of example and in terms of the specific embodiments, it is to be understood that the invention is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. A method for use in flattening an image across a usable field of view in an imaging system having an illumination source configured to illuminate a sample platform with illumination at a first frequency and a detector system having a detector that detects illumination at a second frequency by correcting the image for fluorescence spatial variations and scatter spatial variations, the method comprising:
   acquiring a first image of a stable fluorescent target located proximal to the sample platform using the detector, wherein the stable fluorescent target absorbs illumination at said first frequency and emits at said second frequency and has a size that fills at least a usable field of view of the detector system;
   acquiring a second image of a scattering target located proximal to the sample platform using the detector, wherein the scattering target scatters illumination at said first frequency and has a size that fills at least the usable field of view of the detector system;
   determining a pixel remapping function based on the acquired first and second images; and
   storing the pixel remapping function for later use in correcting for fluorescence spatial variations and scatter spatial variations in images of a sample taken using the imaging system.

2. The method of claim 1, further including acquiring an image of a sample located proximal to the sample platform; and thereafter
   adjusting, on a pixel-by-pixel basis, an intensity value of each pixel in the image of the sample using the pixel remapping function to form a corrected image.

3. The method of claim 2, wherein the pixel remapping function is a piecewise continuous function having first and second linear slopes meeting at a threshold value, wherein adjusting includes:
   using the first slope to modify the pixel value if the intensity value of the pixel is below the threshold value; and
   using the second slope to modify the pixel value if the intensity value of the pixel is above the threshold value.

4. The method of claim 3, wherein the first slope represents an adjustment for scatter spatial variation and wherein the second slope represents an adjustment for fluorescence spatial variations.

5. The method of claim 2, further including displaying a representation of the corrected image.

6. The method of claim 1, wherein the detector includes a two dimensional array detector.

7. The method of claim 6, wherein the array detector includes CCD detector.

8. The method of claim 1, wherein the detector includes a single dimension array detector and wherein acquiring an image includes scanning along a second dimension to build the image.

9. The method of claim 1, wherein the detector includes a single pixel detector and wherein acquiring an image includes scanning along a single dimension or along two dimensions to build the image.

10. A method of flattening an image across a usable field of view in an imaging system having an illumination source configured to illuminate a sample platform with illumination at a first frequency and a detector system that detects illumination at a second frequency, the method comprising:
    acquiring an image of a sample located proximal to the sample platform using the detector;
    accessing stored pixel remapping data for the imaging system, wherein the remapping data includes a mapping function that corrects for fluorescence spatial variations and scatter spatial variations in images taken using the imaging system based on the intensity value of a pixel; and
    adjusting, on a pixel-by-pixel basis, an intensity value of each pixel in the image of the sample using the pixel remapping data to form a corrected image.

11. The method of claim 10, wherein the stored pixel remapping data is determined by:
    acquiring a first image of a stable fluorescent target located proximal to the sample platform using the detector, wherein the stable fluorescent target absorbs illumination at said first frequency and emits at said second frequency and has a size that fills at least a usable field of view of the detector system;

acquiring a second image of a scattering target located proximal to the sample platform using the detector, wherein the scattering target scatters illumination at said first frequency and has a size that fills at least the usable field of view of the detector system; and determining the pixel remapping function based on the acquired first and second images.

12. The method of claim 10, further including displaying a representation of the corrected image.

13. The method of claim 10, wherein the pixel remapping function is a piecewise continuous function having first and second linear slopes meeting at a threshold value, wherein adjusting includes:

using the first slope to modify the pixel value if the intensity value of the pixel is below the threshold value; and using the second slope to modify the pixel value if the intensity value of the pixel is above the threshold value.

14. An imaging system, comprising:

a sample platform;

an illumination source configured to illuminate the sample platform with illumination at a first frequency;

a detector system including a detector element that detects illumination at a second frequency;

a memory that stores pixel remapping data for the imaging system, wherein the remapping data includes a mapping function that corrects for fluorescence spatial variations and scatter spatial variations in images taken using the imaging system based on the intensity value of a pixel; and an intelligence module adapted to receive and process signals from the detector element, wherein during operation, the detector element acquires an image of a sample located proximal to the sample platform, the intelligence module accesses the stored mapping function and adjusts, on a pixel-by-pixel basis, an intensity value of each pixel in the image of the sample using the pixel mapping function to form a corrected image.

15. The system of claim 14, wherein the stored pixel remapping data is determined by:

acquiring a first image of a stable fluorescent target located proximal to the sample platform using the detector, wherein the stable fluorescent target absorbs illumination at said first frequency and emits at said second frequency and has a size that fills at least a usable field of view of the detector system;

acquiring a second image of a scattering target located proximal to the sample platform using the detector, wherein the scattering target scatters illumination at said first frequency and has a size that fills at least the usable field of view of the detector system; and determining the pixel mapping function based on the acquired first and second images.

16. The system of claim 14, wherein the pixel mapping function is a piecewise continuous function having first and second linear slopes meeting at a threshold value, wherein adjusting includes:

using the first slope to modify the pixel value if the intensity value of the pixel is below the threshold value; and using the second slope to modify the pixel value if the intensity value of the pixel is above the threshold value.

17. The system of claim 14, wherein the detector system includes optical elements configured to direct and focus light emitted from or scattered by the sample platform onto the detector element.

18. The system of claim 17, wherein the detector element includes one of a single pixel detector, a one-dimensional detector array or a two-dimensional detector array.

19. The system of claim 17, wherein the detector element includes a CCD detector.

20. The system of claim 14, further including a display device for displaying a representation of the corrected image.

\* \* \* \* \*